(12) United States Patent
Bank et al.

(10) Patent No.: US 7,932,053 B2
(45) Date of Patent: Apr. 26, 2011

(54) METHOD FOR PREPARING MODIFIED COLLAGEN OUTSIDE A HOST CELL

(75) Inventors: Rudolf Antonius Bank, Hoofddorp (NL); Anne-Marie Zuurmond, The Hague (NL); Johannes Petrus M. Jore, Ecken Wiel (NL); Cornelius Antonius M. J. J. van den Hondel, Gouda (NL)

(73) Assignee: Nederlandse Organisatie Voor Toegepast-Natuurwetenschappelijk Onderzoek TNO, Delft (NL)

( * ) Notice: Subject to any disclaimer, the term of this patent is extended or adjusted under 35 U.S.C. 154(b) by 306 days.

(21) Appl. No.: 11/547,822

(22) PCT Filed: Apr. 7, 2005

(86) PCT No.: PCT/NL2005/000264
§ 371 (c)(1),
(2), (4) Date: Jun. 29, 2007

(87) PCT Pub. No.: WO2005/097829
PCT Pub. Date: Oct. 20, 2005

(65) Prior Publication Data
US 2008/0086782 A1    Apr. 10, 2008

(30) Foreign Application Priority Data

Apr. 8, 2004  (EP) .................................... 04076096

(51) Int. Cl.
C12P 21/00   (2006.01)
(52) U.S. Cl. ...................................................... 435/68.1
(58) Field of Classification Search .................. 435/68.1
See application file for complete search history.

(56) References Cited

FOREIGN PATENT DOCUMENTS
WO    WO-03/087343    10/2003

OTHER PUBLICATIONS

Beck et al, (JBC, 271(35): 21566-21573, 1996.*
Eck et al , Goodman & Gilman's The Pharmacological basis of Therapeutics, McGraw-Hill, New York, NY. pp. 77-101.*
Myllyla et al (J Cell. Physiol. 212: 323-329, 2007.*
Sipila et al (Thesis: Faculty of Science, Academic dissertation to be presented, with the assent of the Faculty of Science of the University of Oulu, for public defence in Raahensal, Linnanmaa, on Mar. 23, p. 1-86, 2007.*
Kolb et al, (Gene, 227: 21031, 1999.*
Sigmund (Arterioscler Throm Vasc Biol 20: 1425-1429, 2000.*
Houdebine et al, (Journal of Biotechnology, 98: 145-160, 2002.*
Whisstock et al, (Quaterly Reviews of Biophysics, "Prediction of protein function from protein sequence and structure", 36(3): 307-340, 2003).*
Chica et al. (Curr Opin Biotechnol. Aug. 2005;16(4):378-84).*
Witkowski et al, (Biochemistry. Sep. 7, 1999;38(36):11643-50).*
Boudko et al., J. Mol. Biol. (2002) 317:459-470.
Bruckner and Prockop, Anal. Biochem. (1981) 110:360-368.
Dölz et al., Eur. J. Biochem. (1988) 178:357.
Engel and Prockop, Annu. Rev. Biophys. Biophys. Chem. (1991) 20:137-152.
Frank et al., J. Mol. Biol. (2001) 308:1081-1089.
Frank et al., J. Biol. Chem. (2003) 278:7747-7750.
Jiang and Ananthanarayanan, J. Biol. Chem. (1991) 266:22960-22967.
Kivirikko and Myllyla, Methods in Enzymology (1982) 82:245-304.
Leikina et al., Proc. Natl. Acad. Sci. USA (2002) 99:1314-1318.
McAlinden et al., J. Biol. Chem. (2003) 278:42200-42207.
Ouzzine et al., FEBS Letters (1996) 399:215-219.
Pakkanen et al., J. Biol. Chem. (2003) 278(34):32478-32483.
Stetefeld et al., Structure (2003) 11:339-346.
Wang et al., Matrix Biology (2002) 21:559-566.
Bachinger et al., Eur. J. Biochem. (1980) 106(2):619-632.
Bachinger, Journal of Biological Chemistry (1987) 262(35):17144-17148.
Chan et al., J. Biochemical & Biophysical Methods (1997) 36:11-29.
International Search Report for PCT/NL2005/000264, mailed on Jul. 5, 2005, 4 pages.
Koivu et al., Journal of Biological Chemistry (1987) 262(13):6159-6164.
Middleton et al., Biochemical Journal (1993) 296(2):511-517.
Ryhanen et al., Biochimica et Biophysica Acta (1974) 343:129-137.
Vuorela et al., EMBO Journal (1997) 16:6702-6712.

* cited by examiner

*Primary Examiner* — Anne-Marie Falk
*Assistant Examiner* — Magdalene Sgagias
(74) *Attorney, Agent, or Firm* — Morrison & Foerster LLP

(57) ABSTRACT

The present invention relates to a method for preparing a modified folded protein, comprising modifying unfolded a-chains comprising a collagenous amino acid sequence and thereafter folding at least part of the modified a-chains into a quaternary protein structure, in particular a helical protein structure. The invention allows for an attractive alternative for making recombinant proteins, such as recombinant collagens and the like, which may be used in a variety of biomedical and other applications.

11 Claims, No Drawings

METHOD FOR PREPARING MODIFIED COLLAGEN OUTSIDE A HOST CELL

CROSS-REFERENCE TO RELATED APPLICATIONS

This application is the national phase of PCT application PCT/NL2005/000264 having an international filing date of 7 Apr. 2005, which claims priority from European application EP 04076096.9 filed 8 Apr. 2004. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 313632002900Seqlist.txt | Oct. 12, 2010 | 919 bytes |

The invention relates to the field of the production of tailor-made collagen molecules and the like.

Collagen, gelatine and modifications thereof are molecules that are widely used in a variety of medical and other applications. Generally, collagen used for these applications is purified from tissues of farm animals such as cows, pigs or chickens. In addition, human tissues can be used as a source. The collagen molecules in these tissues are crosslinked, resulting in insoluble aggregates. In order to obtain soluble collagen, the tissues are treated with proteolytic enzymes. Alternatively, the collagen is not solubilized but is used in its insoluble state.

There are several disadvantages in the use of tissue-derived collagen, especially with respect to medical applications. Production of collagen from human or animal tissues necessitates additional processing as to ensure that the final product is free from pathogenic agents such as viruses (like HIV and hepatitis) and prions. Furthermore, sources for purified human collagen are limited. A further complication in the use of collagen that is not species-matched is the induction of an immune response. To overcome immunological reactions, the telopeptides are often removed by proteinases, resulting in the less immunogenic "atelocollagen".

Collagen occurs naturally in a number of genetic types, the most common in terms of abundancy being collagen types I, II, III and IV. Tissues contain mixtures of collagen types, each type having different physicochemical properties. It is rather difficult to obtain a specific genetic collagen type in a homogenous form, i.e. preparations containing the required collagen type is usually contaminated with other genetic types.

Collagen molecules in tissues are normally crosslinked with one another. Collagen molecules can be crosslinked with neighbouring collagen molecules from the same genetic type (e.g. collagen type I×collagen type I), or with collagen molecules from another genetic type [J. J. Wu & D. R. Eyre, 1984, Biochemistry, 23: 1850-1857; J. J. Wu et al., 1992, J. Biol. Chem., 267: 23007-23014; J. J. Wu & D. R. Eyre, 1995, J. Biol. Chem., 270: 18865-18870; C. Nyibizi & D. R. Eyre, 1994, Eur. J. Biochem., 224: 943-950]. The resulting collagen fibrils can be from the same genetic collagen type, but are usually built up from more than one collagen type.

Native collagen is solubilized by enzymes capable of cleaving a peptide bond C-terminal of the crosslinked N-telopeptide amino acid or N-terminal of the C-telopeptide amino acid. It should be stressed that, with the use of enzymes, the crosslink with its surrounding telopeptidyl amino acids remains attached to the triple helical part of the α-chain, even after enzymatic treatment [J. J. Wu & D. R. Eyre, 1984, Biochemistry, 23: 1850-1857].

Collagen solubilized from fibrils containing two or more collagen types will thus obtain pieces of telopeptides from collagen from one genetic type attached to the triple helix of another genetic type. Furthermore, the pieces of telopeptides attached to the triple helix likely affects the reconstitution of fibrils from monomeric collagen molecules.

Crosslinked molecules have a long half-life. This makes the molecules susceptible to non-enzymatic glycation, resulting in collagenous molecules with various prosthetic groups with immunogenic properties [K. M. Reiser, 1998, Proc. Soc. Exp. Biol. Med., 218: 23-37; D. R. Sell et al., 1991, Diab. Metab. Rev., 7: 239-251]. These prosthetic groups cannot be removed, adding an additional problem when one wishes to make preparations containing homogenous collagen molecules.

In order to modify the properties of collagen, the triple helical part of the collagen molecule and the telopeptides may be modified by means of a variety of enzymes. Examples of such modifications are the hydroxylation of proline residues in the triple helix, the hydroxylation of lysine residues in the triple helix and the telopeptides, the addition of a galactose on hydroxylysine residues located in the triple helix, the addition of a glucose on galactosylhydroxylysine residues, and the formation of an aldehyde on the lysine or hydroxylysine residue in the telopeptides. The conversion of a proline into hydroxyproline is catalysed by prolyl hydroxylase, the conversion of lysine into hydroxylysine is catalyzed by lysyl hydroxylase, and the conversion of lysine or hydroxylysine into allysine or hydroxyallysine is catalyzed by lysyl oxidase. Prolyl hydroxylation and lysyl hydroxylation occurs intracellularly during the period that the α-chains are not in a triple helical conformation. Hydroxylation is abolished when the α-chains are folded into a triple helix. In contrast, lysyl oxidase requires collagen molecules that are in a triple helical format and that are clustered together, a situation that occurs essentially extracellularly. The allysine and hydroxyallysine residues in the telopeptides are involved in crosslinking.

All said modifications have an impact on the physicochemical properties of collagen molecules and the fibrils derived from said collagen molecules. Such properties can be benefited from in a variety of applications. However, collagen derived from tissues is already posttranslationally modified, and therefore cannot conventionally be altered anymore in a tailor-made way. For example, hydroxyproline and hydroxylysine cannot conventionally be reversed into proline and lysine, allysine derived crosslinks cannot conventionally be converted into hydroxyallysine derived crosslinks, and allysine and hydroxyallysine cannot conventionally be reversed into lysine and hydroxylysine. Galactose and glucose molecules cannot conventionally be added to hydroxylysine without denaturing the triple helix. Denaturation is also required when one wishes to hydroxylate additional proline and lysine residues.

Clearly, collagen derived from tissues are not ideally suited for use in e.g. medical products. Therefore, quite some effort has been carried out to develop suitable systems expressing human recombinant collagen. Advantages of recombinant production of human collagen are:
- the molecules are of a single genetic type (or a well-defined mixture of genetic types)
- the molecular composition is well-defined since the molecules are typically not modified
- the telopeptides remain intact
- the telopeptides are not crosslinked
- there are no prosthetic groups present, such as non-enzymatic glycation products
- the collagen can be produced in a highly reproducible way
- the alleviation of viral- and prior-related hazards that are associated with the use of collagen derived from animal and/or human tissues.
- the alleviation of immunological responses that are associated with the use of non-human derived sequences
- there is no intrinsic shortage problem
- the collagen is normally not modified, making it possible to modify it as requested
- sequences can be removed or added, resulting in collagen molecules showing different characteristics. Examples are substitution of the amino acid of the collagenase-sensitive cleavage, or the substitution of amino acids involved in crosslinking, or the substitution of amino acid sequences that play a role in protein binding.

Expression of recombinant human (pro)collagen genes have been carried out with mouse 3T3 and 3T6 cells as well as human kidney tumour cells (HT-1080) and human embryonic kidney cells (HEK-293). A disadvantage is the low production level, the high costs associated with culturing mammalian cells, and the fact that these cells produce endogenous collagens as well, the latter making the purification of recombinant collagen more troublesome. In addition to mammalian cell cultures, insect cells (Sf9 or High Five=H5; Invitrogen) have been used for the production of recombinant procollagen. Said cells secrete substantially less non-recombinant procollagen then the above mentioned mammalian cells [M. Tomita et al., 1995, Biochem. J., 312: 847-853; M. Tomita et al., 1997, J. Biochem., 121: 1061-1069]. Procollagen is hydroxylated both in mammalian cells and insect cells; in some cell systems, even an overmodification is seen [A. E. Geddis & D. J. Prockop, 1993, Matrix, 13: 399-405]. In insect cells, co-expression with prolyl 4-hydroxylase and/or lysyl hydroxylase was carried out to increase modification [A. Lamberg et al., 1996, J. Biol. Chem., 271: 11988-11995; M. Nokelainen et al., 1998, Matrix Biol., 16:P 329-338].

Higher production levels of recombinant collagen can be achieved with prokaryotes, lower eukaryotes, and transgenic animals and plants. The host *Escherichia coli* has the disadvantage that repetitive sequences (as is the case with collagen) are prone to recombigenic events, that is, the repetitive DNA sequence is subject to rearranging events resulting in alterations of the original sequence. In addition, *E. coli* does not secrete proteins efficiently into the medium, thus requiring tedious purification protocols carried out in cell lysates. The collagen is not modified. More convenient are yeasts, in particular taxa from the genera *Saccharomyces, Pichia* and *Hansenula* [J. Myllyharju et al., 2000, Biochem. Soc. Transactions, 28: 353-357; P. D. Toman et al, 2000, J. Biol. Chem., 275: 23303-23309; E. C. de Bruin, 2002, FEMS Yeast Research, 1:291-298]. Transgenic silkworms, mammalians and plants also allow the production of high quantities of recombinant collagen [M. Tomita et al., 2003, Nature Biotechnology, 21: 52-56; N. J. Bulleid et al., 2000, Biochem. Soc. Transactions, 28: 350-353; P. D. Toman et al., 1999, Transgenic Research, 8: 415-427; D. C. A. John et al., 1999, Nature Biotechnology, 17: 385-389; F. Ruggiero et al., 2000, FEBS Letters, 469: 132-136; S. Perret et al., 2001, J. Biol. Chem., 276: 43693-43698]. Generally no modifications of collagen (such as prolyl hydroxylation) are seen in such systems, being the reason that complex recombinant systems have been developed to achieve the desired modifications. This has been done in yeasts, and in transgenic animals and plants. In all cases, modification of collagen is always achieved within the cell, normally by means of an expression vector comprising a sequence encoding a collagen in combination with a second expression vector comprising a sequence encoding a collagen-modifying enzyme. In the case of prolyl hydroxylase two such vector systems are needed, as the enzyme is a tetramer built up from two different proteins. Disadvantages of the co-expression of prolyl-4-hydroxylase are that it puts a higher strain on the yeast (resulting in decreasing efficiencies of transformation), and that lower amounts of collagen are produced [A. Vuorela et al., 1997, EMBO J 16: 6702-6712; I. Keizer-Gunninl et al., 2000, Matrix Biology 19:29-36]. Apart from that, the level of prolyl hydroxylation cannot be regulated, and complete hydroxylation levels have never been achieved. This results in collagen molecules with a lower thermal stability compared to collagen normally found in tissues.

In summary, none of the recombinant systems described so far are able to generate tailor-made modified, triple helical, collagen molecules in a convenient way.

It is an object of the present invention to provide an alternative method for preparing a modified folded collagenous protein, in particular a modified helically shaped protein such as a modified collagen or a modified gelatine. In particular it is an object of the invention to provide such a method that allows a convenient preparation of tailor-made folded modified collagenous proteins with specific physicochemical characteristics.

It has now surprisingly been found that it is possible to prepare a modified folded collagenous protein outside a cell.

Accordingly, the present invention relates to a method for preparing a modified folded collagenous protein, comprising the extracellular modification of unfolded polypeptide chains (such as α-chains), which preferably comprise a collagenous amino acid sequence. and thereafter folding at least part of the modified chains into a quaternary protein structure.

In particular, the present invention relates to a method for the production of a modified collagenous protein, comprising providing unfolded collagen α-chains comprising an association domain; modifying the unfolded α-chains outside a host cell; and folding the modified α-chains into a triple helical structure.

More in particular the invention respectively relates to the production of:
- modified recombinant collagen comprising: synthesis of an association domain-containing recombinant collagenous protein by a host cell, unfolding of the triple helical structure (thereby forming unfolded α-chains), enzymatically modifying the unfolded α-chains outside the host cell, and refolding the α-chains into a triple helical collagenous molecule.
- modified recombinant gelatin comprising: synthesis of an association domain-containing recombinant collagen by a host cell, unfolding of the triple helical structure, enzymatically modifying the α-chains outside the host cell, and refolding the α-chains into a gelatin-like structure.
- enzymatically modified recombinant gelatin comprising: synthesis of recombinant collagen by a host cell, unfolding of the triple helical structure, enzymatically modifying the α-chains outside the host cell, and refolding the α-chains into a gelatin-like structure.

modified recombinant gelatin comprising: synthesis of a polypeptide with a collagenous sequence by a host cell, unfolding of the triple helical structure, enzymatically modifying the α-chains outside the host cell, and refolding the α-chains into a gelatin-like structure.

modified recombinant gelatin comprising: synthesis of a polypeptide with a collagenous sequence by a host cell and enzymatically modifying the α-chains outside the host cell.

The present invention allows convenient preparation of the modified collagenous protein, starting from well-defined protein preparations, such as collagen preparations, containing molecules with predefined characteristics. In particular, it simplifies the production of tailor-made folded modified collagenous proteins with specific physicochemical characteristics.

A method according to the invention no longer requires the development of cumbersome protocols would hare to be developed to effect the required posttranslational modification of recombinant collagen within the cell. Such development would be required due to the multiplicity of posttranslational modifications to which the polypeptide chain, such as the α-chain of procollagen and collagen is subjected in intracellular modification.

The invention is based on the surprising insight, that triple helical collagen containing a nucleation point can be unfolded and subsequently be refolded in a triple helix in a high yield. The unfolded α-chains are modified by contacting the soluble preparation with collagen-modifying enzymes. The amount of modification can be varied by simple parameters such as the reaction time and/or the amount of enzyme. The type of modification can be varied by varying the type of collagen-modifying enzymes present in the contacting solution.

The invention offers several advantages. For instance, only a single collagen-producing host is required for generating a variety of collagen molecules each displaying certain characteristics. The same collagen-modifying enzyme preparations can be used for modifying a variety of genetic collagen types produced by different collagen-producing hosts. Thus, a versatile system is obtained for preparing tailor-made collagen molecules for a number of applications, such as biomaterials for tissue engineering or drug/gene delivery systems.

It is surprising that the modification outside the cell is possible. It has been commonly known for decades that— outside a cell—collagen molecules can easily be unfolded (e.g. by increasing the temperature), but generally do not correctly refold in a triple helix anymore, even under optimal conditions. In practice, hydroxylation of proline residues, hydroxylation of lysine residues, and the glycosylation of hydroxylsine residues occurs only on unfolded α-chains. Once the α-chains are folded into a triple helical configuration, the α-chains are not recognized anymore by the enzymes, meaning that said modification reactions do not occur anymore once the collagen molecule is in its native form. Thus, collagen molecules are folded within the cell, and only the folded collagen molecules are secreted into the extracellular space. For this reason modifications, e.g. hydroxylation of proline residues of recombinant collagen, are conventionally carried out within the cell by means of co-expression of prolyl hydroxylase.

It has already been published that unfolded collagen molecules can, under certain conditions, refold into a perfectly matched triple helical molecule in high yields. This has been reported to be possible for collagen type III, but not for collagen type I or collagen type II. Collagen type III contains, in contrast to collagen type I and II, per α-chain two adjacent Cys residues, the first Cys being the end of the triple helical sequence and the second Cys being the start of the C-telopeptide. These Cys residues form disulfide bonds between the three α-chains, and keep the chains in exact register after unfolding. Such an association domain highly facilitate s the refolding of the unfolded α-chains into a triple helix [Bächinger et al., 1980, Eur. J. Biochem., 106:619-632; J. Engel & D. J. Prockop, 1991, Annu. Rev. Biophys. Biophys. Chem., 20: 137-152]. In the case of collagen type III, the association domain is composed of the two Cys residues present at the C-terminal end of the molecule. Of course, other association domains are possible. In collagen type IV, a proper folding of the denatured α-chains into a triple helix can be achieved under conditions that keeps the C-terminal globular NC1-domain intact [R. Dölz et al., 1988, Eur. J. Biochem., 178: 357]. In this case, the NC1-domain serves as the association domain. Despite the existence of association domains being known for more than two decades, the existence of association domains in the preparation of modified folded proteins has never been taken into consideration in the art.

So far, it has not been considered to modify the collagen molecule outside the cell, which is fundamentally different. It is thought that this has not been considered because it is generally assumed in the art that the modified chains cannot be returned into a correctly aligned triple helix. It is a surprising insight that it is possible to modify α-chains, preferably comprising a collagenous amino acid sequence, and thereafter fold them into a more or less natural structure such as the triple-helical structure of collagen, a gelatin structure or a gelatin-like structure, outside of a living organism.

This offers a tremendous advantage, as a method according to the invention is highly versatile, since a single source of α-chains—preferably in the form of a collagen—can be used for a variety of modified collagenous proteins, whereas conventional recombinant methodologies require the technically difficult co-expression with collagen-modifying enzymes inside the host-cell. Unlike in the present invention, this leads to the need for a different host-cell for each different type of modified protein.

The invention has been found very suitable for the production of collagen and collagen-like compounds comprising for instance different combinations of hydroxylated proline en lysine residues and glycosylated hydroxylysine residues, wherein said modifications are carried out outside the cell. Different combinations will lead to different material properties, to be explored in different applications. The term "collagenous" as used herein refers to a polypeptide having the same or similar primary or secondary or tertiary structure as collagen or gelatin.

The invention thus provides an attractive method for preparing a modified collagenous protein, which may be used advantageously in a number of applications, such as biomaterials for tissue engineering or drug/gene delivery systems.

In particular, the invention provides a method for the production of recombinant collagen in a triple helical format in a host cell, the unfolding of the collagen, the modification of the α-chains by a collagen-modifying enzyme outside the host cell, and the refolding of the α-chains into a triple helix (also outside the host cell).

The term "α-chain comprising a collagenous amino acid sequence" as used herein is defined as a polypeptide capable of forming an α-helix and preferably comprising stretches of a repetitive Gly-X-Y sequence (where X and Y can be any amino acid). Preferably, at least about 60% of the polypeptide is formed of Gly-X-Y stretches. Thus, preferably at least about 20% of the amino acid residues in the polypeptide are glycine residues.

The term "quaternary protein structure" as used herein is defined as a protein formed of at least two polypeptide chains. In particular, the term is used for describing a protein formed of two or more polypeptide chains that are at least partially folded into a helical structure, such as a helical structure of two α-chains (or parts thereof) forming a double helical structure or of three α-chains (or parts thereof) forming a triple helical structure.

The chains are optionally covalently bound at one or more sites.

An example of a quaternary protein structure is collagen, which is typically formed of three α-chains wound together in a helical structure.

Another example of a quaternary protein structure is gelatin. In gelatin not all of the α-chains are wound together in a helical structure. Rather gelatin is formed of partially folded α-chains, which typically form relatively short segments of triple helices at random positions in the structure.

The term "unfolded" as used herein means that at a substantial part of the moiety (such as the α-chain) is dissociated from other moieties (such as other α-chains), with which it may form a quaternary protein structure end/or that at least a substantial part of the moiety is unwound from its natural structure (such as the α-helix). In particular the term is used to indicate that at least the majority is dissociated and/or unwound. More in particular, the term is used to indicate that the whole chain is dissociated and/or unwound, preferably with the exception of a nucleation point (such as an association domain, see below) that holds several chains together.

The unfolded α-chains may still be attached (covalently or non-covalently) to one another at a limited number of amino acid residues, which attached section may serve as a nucleation point for the refolding after modification of the α-chains. The number of amino acid residues to which the unfolded chains may be attached is in practice generally in the range of 1-50, preferably 2-30.

The source for the α-chains may be any available source. Preferably the α-chains are provided by unfolding a collagen, in particular a recombinant collagen, preferably a recombinant human collagen. The collagen may be obtained as known in the art, e.g. as described in any of the publications cited herein. Preferred types of collagen include the fibrillar collagens (types I, II, III, V, XI) and FACIT collagens (types IX and XII).

The source for the α-chains, such as the collagen, may be obtained from a prokaryotic cell or from a eukaryotic cell. Preferred examples of prokaryotic cells include bacterial cells, in particular from the genera *Escherichia*, *Lactobacillus*, and *Bacillus*.

Preferred eukaryotic cells include mammalian cells, yeast, fungi and insect cells.

Particularly preferred is a fungus, more preferably a fungus selected from the group consisting of the filamentous genera. Preferred examples thereof are *Aspergillus*, *Trichoderma*, *Acremonium*, *Cryphonectria*, *Cochliobolus*, *Neurospora*, *Chrysosporium*, *Fusarium*, *Trametus* and *Schizophyllum*. Fungi are particularly interesting for industrial recombinant protein synthesis, as they show in general high production levels as well as efficient secretion of the proteins.

The host cell may be employed in a culture or as an integral part of a transgenic animal or transgenic plant.

If desired, the skilled person will know how to genetically modify the host cells in order to let it produce the desired source for the α-chains, such as collagen, and how to employ the cells, based upon common general knowledge, the cited prior art and the present description and claims.

It has been found that the folding of the α-chains is positively influenced by the presence of an association domain in the α-chains, i.e. a structure that is capable of acting as a nucleation point from which the folding of the α-chains can be initiated. The association domain may be a moiety that holds the α-chains together at at least one point in the chains even when they are unfolded and/or a moiety that brings the unfolded α-chains together in each others vicinity at the moment the folding is started. In both cases, the unfolded α-chains are folded into a quaternary structure, such as a triple helix of three α-chains in the case of a collagen, starting from the association domain. More in particular, an association domain may be a structure that holds the three α-chains together even when they are unfolded, and/or as a structure that brings unfolded α-chains together in each other's vicinity. In both cases, the unfolded α-chains are refolded into a triple helical molecule once the parameter that caused unfolding is removed or rendered ineffective. As such, an association domain can be a stretch of amino acids, Cys-Cys bridges between α-chains, or intramolecular crosslinks between α-chains. In collagen biochemistry, the term "intramolecular crosslink" is commonly used to refer to crosslinks between α-chains of a collagen molecule.

These findings can be used in an advantageous way in this invention. It allows constructing a vector containing a collagenous sequence comprising two Cys residues. By placing the two Cys residues in collagen type I and collagen type II, for example at analogous positions as those normally seen in collagen type III, collagen molecules are obtained that can be unfolded followed by refolding into a triple helix. This unprecedented feature that is created by the addition of the association domain makes it possible to enzymatically modify the collagen molecules in a tailor-made way with collagen-modifying enzymes such as prolyl hydroxylase and lysyl hydroxylase. The advantages are obvious: the propeptides are omitted (thus achieving higher production levels and omitting treatments with proteinases that are necessary for removing the propeptides), and a single collagen-producing host is required for the production of a set of collagen molecules showing different physicochemical properties (as the collagen molecules can be contacted now with different sets of collagen-modifying enzymes outside the cells, resulting in native collagen molecules with different but well-defined combinations/levels of modifications). The resulting collagen preparations can be used for a variety of applications, such as the preparation of tailor-made biomaterials for tissue engineering purposes, or as materials for drug/gene delivery systems.

The association domain may comprise a covalent bond between the α-chains, which substantially remains intact when the α-chains are unfolded and when they are being modified. A preferred example of such a covalent bond is a bond formed by two Cys residues. Such a bond is for instance naturally present in collagen type III. Collagen type III contains per α-chain two adjacent Cys residues at the C-terminal end of the molecule, the first Cys being the end of the triple helical sequence and the second Cys being the start of the C-telopeptide. These Cys residues form disulfide bonds between the three α-chains, and keep the chains in exact register after unfolding. Such an association domain highly facilitates the refolding of the unfolded α-chains into a triple helix e.g. under conditions described in the art [Bächinger et al., 1980, Eur. J. Biochem., 106:619-632; J. Engel & D. J. Prockop, 1991, Annu. Rev. Biophys. Biophys. Chem., 20:137-152].

The two Cys residues may be adjacent to another or spaced relatively far apart, e.g. separated up to 25 residues. The Cys residues may be present in any section of the α-chains. In particular they may be present in the section of the α-chain forming part of the triple-helix (when folded into collagen), the telopeptide part of the α-chain, the propeptide part of the α-chain, at the start of the α-chain and/or at the end of the α-chain.

Another example of a suitable association domain is the NC-1 domain, as can be found in collagen type IV, which allows a proper folding of the denatured α-chains into a triple helix under conditions that keep the C-terminal globular NC1-domain intact [see e.g. R. Dölz et al., 1988, Eur. J. Biochem., 178: 357].

Another type of association domains is formed by the association domains comprising an amino sequence that is able to keep the α-chains together by non-covalent bonding (such as electrostatic forces or hydrogen bonding). Such domain is typically a section of the α-chain having a higher melting temperature (unfolding temperature) than the remainder of the α-chain, such at a temperature above the melting temperature of (majority of the α-chain) the chains remain attached to one another at that section. The melting temperature or unfolding temperature as used herein is the value as determined by the proteolytic degradability of the molecule [P. Bruckner & D. J. Prockop, 1981, Anal. Biochem., 110: 360-368] or by physical methods such as circular dichroism or differential scanning calorimetry [E. L. Leikina et al., 2002, Proc. Natn. Acad. Sci. USA, 99: 1314-1318] The melting temperature or unfolding temperature of such an association domain is preferably at least 5° C. higher than that of the remainder of the protein, more preferably 5 to 30° C. higher.

An example of an association domain which holds together chains by non-covalent bonding is an amino acid sequence known as "foldon", a 27-amino acid stretch located at the C-terminal part of the bacteriophage T4 fibritin [S. Frank et al., 2001, J. Mol. Biol., 308: 1081-1089; S. Boudko et al., 2002, J. Mol. Biol., 317: 459-470; J. Stetefeld et al., 2003, Structure, 11: 339-346]. The amino acid sequence of foldon is GYIPEAPRDGQAYVRKDGEWVLLSTFL (SEQ ID NO:1).

Foldon has a high degree of thermal stability. The unfolding temperature of foldon is about 90° C., which is much higher than the unfolding temperature of collagen (normally below 50° C.). With molecular biology techniques, which are known per se, the foldon sequence or an analogue thereof can be placed in an amino acid sequence, such as a collagen sequence, preferable at the C-terminal part of said collagen sequence. The skilled person will know how to employ such method, based upon routine knowledge, the information disclosed herein and e.g. the two cited references, describing suitable methods for placing foldon at the C-terminus of a collagenous sequence consisting of [GlyProPro]$_{10}$. In another reference, it is shown that foldon can also be placed at the N-terminus of [GlyProPro]$_{10}$, and that in this case triple helix nucleation is initiated at the N-terminus [S. Frank et al., 2003, J. Biol. Chem., 278:7747-7750]. Recently, the foldon sequence has been used as an effective oligomerization domain for the assembly of recombinant triple helical collagen type I and III molecules in the yeast *Pichia pastoris* as a substitute for the C propeptide [O. Pakkanen et al., 2003, J. Biol. Chem.].

Any of these described methods described in the art can be used to provide a source for the α-chains to be modified in accordance with the invention. The skilled person will know how to amend the described procedures for carrying out the present invention, based upon common general knowledge and the information disclosed herein.

It has been found that the use of a foldon or a foldon-analogue is highly advantageous in a recombinant system wherein a correct alignment of the three α-chains in the absence of the foldon or foldon-analogue is somehow troublesome. Incorrect alignment would be detrimental to a correct refolding of the α-chains.

Accordingly, the invention also relates to a method wherein the association domain comprises an amino acid sequence that is able to refold after denaturation and that is able to correctly register the individual α-chains such that triple helical formation is initiated. Often, such amino acid sequences show α-helical coiled-coil motifs [A. McAlinden et al., 2003, J. Biol. Chem., 278: 42200-42207].

It has further been found that foldon or a foldon analogue in a collagen molecule tends to tighten the three individual α-chains together at conditions that unfold the triple helical structure of collagen. Thus, unfolding and refolding of collagen can be performed in conditions other than heating and subsequent cooling of the solution.

It has further been found that a collagenous sequence containing a foldon sequence or an analogue thereof has a higher thermal stability than a collagenous sequence without the foldon sequence.

This is of interest for recombinant collagens showing a low thermal stability, e.g. due to the lack of hydroxyproline residues.

Other examples of sequences that can be used as an association domain in accordance with the invention, have been identified in a number of collagenous proteins [A. Snellman et al., 2000, EMBO J., 19: 5051-5059; S. Areida et al., 2001, J. Biol. Chem., 276: 1594-1601; M. Mazzorana et al., 2001, J. Biol. Chem., 276: 27989-27998; Y. Zhang & Q. Chen, 1999, J. Biol. Chem., 274: 22409-22413; A. McAlinden et al., 2002, J. Biol. Chem., 277: 41274-41281; A. McAlinden et al., 2003, J. Biol. Chem., 278: 42200-42207; A. Lesage et al., 1996, Biochemistry, 35: 9647-9660; D. E. Mechling et al., 1996, J. Biol. Chem., 271: 13781-13785; D. E. Mechling & H. P. Bächinger, 2000, J. Biol. Chem., 275: 14532-14536]. These are also in particular suitable for the association and proper trimeric assembly of the α-chains into a collagen, some of them show a high denaturation temperature. Most of the sequences derive from the non-collagenous domains of a wide range of collagen types, but coiled-coil domains of other proteins (such as the collectin family) are suitable candidates as well.

Preferable, human sequences should be used for the association domain. This is thought to be advantageous because immunological reactions are expected to be absent or very mild.

Optionally, an association domain may be removed from the modified folded quaternary protein structure. If removal may be desired, one may opt to provide α-chains comprising an association domain sequence and a proteinase-sensitive cleavage site. The cleavage site may that suitably be situated between the sequence of the association domain and the collagen molecule. Thus said cleavage site can be clipped by contacting it with the appropriate enzyme. Examples of suitable cleavage sites are sequences which are normally not present in collagenous proteins. Examples of such sequences are sequences recognized by e.g. thrombin (Leu-Val-Pro-Arg-Gly-Ser), enterokinase (Asp-Asp-Asp-Asp-Lys), tobacco etch virus (Glu-Asn-Leu-Tyr-Phe-Gln-Gly) or factor Xa protease (Ile-Glu-Gly-Arg).

An α-chain comprising any of the above mentioned types of association domains can be made by a standard recombinant DNA technique, involving the incorporation of the code for the appropriate amino acid sequence in the DNA of a host cell. Suitable techniques include those described by J. Sambrook & D. W. Russell [2001, Molecular Cloning. A laboratory manual. Third edition. Volume 1+2+3. Cold Spring Harbor, N.Y.].

Another structure that can be used as an association domain is a crosslink. Methods have been disclosed in the art to introduce, e.g. by a chemical method, crosslinks in proteins, in particular in soluble, triple helical collagen molecules. Examples of crosslink methods are the use of glutaraldehyde, cyanamide, 1-ethyl-3(-3 dimethyl aminopropyl) carbodiimide hydrochloride, disuccinimidyl glutarate, polyepoxy compounds, or reducing sugars (Maillard reaction) [S. Perret et al., 2001, J. Biol. Chem., 276: 43693-43698; S. F. Badylak, 2002, in: A. Atala & R. P. Lanza (eds.), Methods of tissue engineering, Academic Press: 505-514].

The unfolding of the source for the α-chains, for instance a quaternary protein structure such as the (recombinant) collagen, may suitably take place in vitro by subjecting the quaternary protein structure to a temperature above the unfolding temperature of said structure, and in case a non-covalently bound association domain is present, preferably below the melting temperature unfolding temperature of the association domain.

Very good results have been achieved with a method wherein the unfolding takes place at a temperature in the range of 30 to 48° C. at pH 6-8. The unfolding preferably is carried out in phosphate buffered saline (PBS) with a protein (collagen) concentration of 0.5-2.5 mg/ml, although other reaction media and or protein concentrations may be used.

The unfolded α-chains may suitably be modified by any means known in the art, and preferably by contacting a liquid preparation (e.g. a solution or dispersion) with at least one modifying enzyme, thereby causing a preferably covalent modification of the chemical nature of the α-chains. In a preferred embodiment, the modification takes place in or on amino acid side chains of the unfolded α-chains. Thus, the invention encompasses a method for modifying amino acid side chains of unfolded α-chains.

The modification degree can be chosen in a wide range, depending on the type of application for which the modified molecules are intended to be used. The reaction conditions can routinely be determined based upon the nature of the α-chains, the reagents (such as enzymes and cofactors), the desired degree of modification. The skilled person will know how to choose suitable conditions such as the reaction time and/or the amount of enzyme.

The type of modification can be varied by varying the type of modifying enzymes present in the contacting liquid.

For instance hydroxylation of proline residues, hydroxylation of lysine residues, and/or the glycosylation of hydroxylysine residues can enzymatically be performed on the unfolded α-chains, whereas such modifications cannot be carried out once the α-chains are folded into a triple helical configuration, the form in which they are usually secreted by collageni producing cells.

Preferred examples of modifying enzymes include enzymes selected from:

Prolyl-4-hydroxylases (e.g. P4H; EC 1.14.11.2; procollagen proline, 2-oxoglutarate 4-dioxygenase); purpose: 4-hydroxylation of proline in the sequence Gly-X-Pro-Gly, wherein "X" can be any amino acid residue.

Prolyl-3-hydroxylases (e.g. P3H; EC 1.14.11.7; procollagen proline, 2-oxoglutarate 3-dioxygenase); purpose is 3-hydroxylation of proline in the sequence Gly-Pro-4Hyp-Gly.

Helical lysyl hydroxylase (e.g. HLH; EC 1.14.11.4; procollagen lysine, 2-oxoglutarate 5-dioxygenase=PLOD) for the: 5-hydroxylation of lysine in the sequence Gly-X-Lys-Gly, wherein "X" can by any amino acid residue.

Telopeptide lysyl hydroxylase (e.g. TLH; EC 1.14.11.4; procollagen lysine, 2-oxoglutarate 5-dioxygenase=PLOD); for the 5-hydroxylation of lysine in the N-telopeptides and/or C-telopeptides.

Hydroxylysyl-galactosyltransferases (e.g. EC 2.4.1.50; UDP galactose: 5-hydroxylysine-collagen galactosyltransferase); for transfer of galactose (O-glycosylation) to 5-hydroxylysine in the sequence Gly-X-Hyl-Gly, wherein X can be any amino acid residue.

Galactosylhydroxylysyl-glucosyltransferases (e.g. EC 2.4.1.66; UDP glucose: 5-hydroxylysine-collagen glucosyltransferase); for transfer of glucose (O-glycosylation) to galactosylhydroxylysine in the sequence Gly-X-GalHyl-Gly, wherein X can be any amino acid residue.

Lysyl oxidases (e.g. LOX, LOXL, LOXL-2, LOXL-3 and LOXL-4; EC 1.4.3.13; protein lysine 6-oxidase); for oxidative deamination of the ε-amino group in telopeptidyl lysine and telopeptidyl hydroxylysine residues. The corresponding aldehydes are known under their trivial names allysine and hydroxyallysine, respectively.

Suitable methods for modifying unfolded α-chains or other peptide sequences by said enzymes are disclosed in a variety of papers [prolyl hydroxylase and lysyl hydroxylase: K. I. Kivirikko & R. Myllylä, 1982, Methods in Enzymology, 82: 245-304; P. Jiang & V. S. Ananthanarayanan, 1991, J. Biol. Chem., 266: 22960-22967; hydroxylysyl-galactosyltransferase and galactosylhydroxylysyl-glucosyltransferase: K. I. Kivirikko & R. Myllylä, 1982, Methods in Enzymology, 82: 245-304; C. Wang et al., 2002, Matrix Biology, 21: 559-566; lysyl oxidase: M. Ozzuni, A. Boyd & D. J. S. Hulmes, 1996, FEBS Letters, 399: 215-219].

The enzyme(s) may be of natural origin or made by recombinant technology.

After modifying the α-chains, the chains are folded into the quaternary protein structure, preferably a triple-helical structure, such as a collagen triple helix structure, a gelatin structure, a collagen-like structure or a gelatin-like structure.

In principle (re)folding can be accomplished analogously to the manner wherein the unmodified analogues can be refolded after having been unfolded. Suitable conditions are described in the art e.g. in a number of the publications cited above and in Bächinger et al., 1980, Eur. J. Biochem., 106: 619-632; J. Chandrarajan, 1978, Biochem. Biophys. Res. Commun., 83: 180-186; Beier & Engel, 1966, Biochemistry, 5: 2744-2755; S. Perret et al., 2001, J. Biol. Chem., 276: 43693-43698]. In a preferred embodiment, folding or refolding is carried out by setting the temperature to which the modified α-chains are exposed to below 40° C., more preferably below 37° C. If desired, the skilled person will be able to modify the conditions, to fine-tune the refolding, depending upon the exact nature of the modified chains and the desired quaternary structure. A very suitable way of (re)folding the α-chains is a method wherein the temperature is brought below the unfolding temperature. Folding or refolding in a method according to the invention occurs preferably without interference or assistance of cellular organelles.

Despite the advantages and convenience of the described methods, and despite the fact that the described methods are known for more than two decades, the addition of an association domain has so far never been considered in recombinant systems aimed at producing modified collagen. Instead, the technically difficult co-expression with collagen-modifying enzymes has so far been used, and much effort has been put so far in optimalising this complex expression system. This clearly shows the non-obviousness of the present invention.

The invention further relates to novel sequences, proteins, host cells, vectors and the like, obtainable by a method as described herein.

The invention will now be illustrated by the following Examples.

EXAMPLE 1

Expression of Recombinant Helical Lysyl Hydroxylase (PLOD1) in Mammalian Cells

The human PLOD1 signal peptide sequence followed by a His6 tag sequence was linked to the cDNA sequence of human PLOD1 starting from the amino-terminal end of the molecule. Four overlapping oligonucleotides, covering the nucleotide sequence for the PLOD1 signal peptide and a His6 tag flanked by NheI and BamHI restriction sites, were annealed and the protruding 5' ends were filled in by cloned pfu polymerase (Stratagene). The resulting double-stranded, blunt-ended product was ligated to the EcoRV site of the pMOSBlue vector (Amersham). The human PLOD1 cDNA sequence covering nucleotides 55 to 2184 was cloned into the BamHI/EcoRI sites of the construct. Finally, an expression construct was created by cloning the PLOD1 cDNA sequence including the signal peptide and the His6 tag into the NheI/EcoRI site of pcDNA3.1(–) (Invitrogen). The expression construct, called pDHLH.1, was checked by sequencing. The recombinant HLH protein contains a His6 tag at the N-terminus after signal peptide cleavage. HEK293 cells were cultured in DMEM supplemented with 10% FBS in 5% CO2 until they reached confluency. For transfection cells were plated in 10 cm2 wells at such a density that 70% confluence was reached after 16 hrs of incubation at 37° C. Two hours prior to transfection, fresh medium was added to the cells. The cells were transfected with a total of 1 mg of each plasmid using the lipid-based FuGENE™ 6 transfection reagent (Roche Molecular Biochemicals, Indianapolis, Ind., USA) in a ratio of 1:4 (mg DNA: ml FuGENE). To obtain stable HEK293 clones expressing HLH the cells were diluted 100 times 24 hours after transfection and plated in 10 cm2 wells in selective medium containing 700 mg/ml geneticine (Invitrogen). After two weeks culturing in selective medium single clones were picked and screened for HLH expression by Western blotting. Considerable amounts of helical lysyl hydroxylase were observed in both the cytosol and in the culture medium. The helical lysyl hydroxylase present in the culture medium was precipitated, dialysed against PBS and used for modification purposes of (pro)collagen.

EXAMPLE 2

Modification of Collagen

In the following experiment collagen type I was modified lysyl hydroxylase. The association domain of collagen was in this case the C-propeptide of collagen type I. This propeptide connects the three α-chains of collagen together by means of Cys-Cys bridges. The method is comparable with the folding/refolding experiments carried out in the past with collagen type III; in this collagen type, the Cys-Cys bridges are located at the C-terminal end of the collagen molecule, between the triple helix and the C-propeptide [Bächinger et al., 1980, Eur. J. Biochem., 106: 619-632; J. Engel & D. J. Prockop, 1991, Annu. Rev. Biophys. Biophys. Chem., 20: 137-152].

Procollagen type I (that did not contain Hyl and only limited amounts of Hyp was obtained from fibroblasts cultured in the presence of a,a'-dipyridyl as described in K. I. Kivirikko & R. Myllylä, 1982, Meth. Enzymol., 82: 245-304). The procollagen was solubilised in PBS pH 7.4 and kept at a temperature of 40° C. Lysyl hydroxylase (obtained as described in Example 1) was added in combination with its co-factors (K. I. Kivirikko & R. Myllylä, 1982, Meth. Enzymol., 82: 245-304).

After an incubation period of 2 h, the solution was slowly cooled to 4° C. in order to refold the triple helix. The amount of hydroxylysine in the preparation was determined by means of amino acid analysis [R. A. Bank et al., 1996, Anal. Biochem., 240: 167-176]. The amount of Hyl was in the order of 30 residues per collagen molecule (whereas the start value was 5 Hyl residues per collagen molecule).

The invention claimed is:

1. A method for the in vitro production of a modified collagenous protein, comprising
   (a) unfolding folded collagen α-chains comprising an association domain to obtain unfolded collagen α-chains;
   (b) modifying the unfolded α-chains by adding modifying enzymes; and (c) folding the modified α-chains into a triple helical structure;
wherein none of steps (a)-(c) is performed intracellularly; and
wherein said association domains comprise one or more interchain crosslinks linking the collagen α-chains together; or
wherein the association domains comprise amino acid sequences that reassociate after unfolding; or
wherein the association domains comprise amino sequences by which the collagen α-chains remain bound to each other during unfolding of the remainder of the collagen α-chains; and
wherein said modifying enzymes modify the amino acid side chains of the α-chains.

2. The method of claim 1, wherein the modifying is by one or more enzymes selected from the group consisting of prolyl hydroxylases, lysyl hydroxylases, lysyl oxidases, hydroxylysyl-galactosyltransferases and galactosylhydroxylysyl-glucosyltransferases.

3. The method of claim 2, wherein the modifying comprises hydroxylating proline by a prolyl-3-hydroxylase, or a prolyl-4-hydroxylase or a combination thereof.

4. The method of claim 2, wherein the modifying comprises hydroxylating lysine by a helical lysyl hydroxylase, or a telopeptide lysyl hydroxylase or a combination thereof.

5. The method of claim 2, wherein the modifying comprises glycosylating hydroxylysine by a lysyl hydroxylase.

6. The method of claim 2, wherein the modifying comprises oxidatively deaminating the ε-amino group of lysine or hydroxylysine by a lysyl oxidase.

7. The method of claim 2, wherein said enzymes are recombinant proteins synthesized by prokaryotic or eukaryotic cells.

8. The method of claim 1, wherein said interchain crosslinks are Cys-Cys bridges wherein said Cys residues are present in the triple helical part of the α-chain and/or in the telopeptide part of the α-chain and/or in the propeptide part of the α-chain and/or at the start of the α-chain and/or at the end of the α-chain.

9. The method of claim 1, wherein said amino acid sequences comprise SEQ ID NO:1.

10. The method of claim 1, wherein said amino acid sequences are present in the triple helical part of the α-chains and/or in the telopeptide part of the α-chain and/or in the propeptide part of the α-chain and/or at the start of the α-chain and/or at the end of the α-chain.

11. The method of claim 1, wherein said crosslinks are formed by at least two Cys residues per collagen α-chain.

* * * * *

```
SEQUENCE LISTING

<160> NUMBER OF SEQ ID NOS: 1

<210> SEQ ID NO 1
<211> LENGTH: 27
<212> TYPE: PRT
<213> ORGANISM: Enterobacteria phage T4
<220> FEATURE:
<221> NAME/KEY: misc_feature
<222> LOCATION: (1)...(27)
<223> OTHER INFORMATION: foldon located at C terminal part
      of bacteriophage T4 fibritin

<400> SEQUENCE: 1

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```